United States Patent [19]

Huber et al.

[11] Patent Number: 5,352,612
[45] Date of Patent: Oct. 4, 1994

[54] METHOD AND APPARATUS FOR THE STEPWISE MOVEMENT OF ITEMS

[75] Inventors: Michael D. Huber, San Juan Capistrano; Stephen L. Frye; John C. Mazza, both of El Toro, all of Calif.

[73] Assignee: Baxter Diagnostics Inc., Deerfield, Ill.

[21] Appl. No.: 15,120

[22] Filed: Feb. 9, 1993

[51] Int. Cl.⁵ .............................................. G06F 15/46
[52] U.S. Cl. .................................... 436/47; 436/43; 436/50; 436/55; 436/807; 422/63; 422/64; 422/67; 364/497
[58] Field of Search ................. 436/43, 47, 50, 55, 436/807; 432/63, 64, 67; 364/497

[56] References Cited

U.S. PATENT DOCUMENTS

| | | | |
|---|---|---|---|
| 3,971,630 | 7/1976 | Sandrock et al. | 436/45 |
| 4,166,094 | 8/1979 | Froehlich et al. | 422/64 |
| 4,678,752 | 7/1987 | Thorne et al. | 435/291 |
| 4,695,430 | 9/1987 | Coville et al. | 422/65 |
| 4,811,764 | 3/1989 | McLaughlin | 141/98 |
| 4,812,858 | 3/1989 | Murray | 346/139 R |
| 4,815,978 | 3/1989 | Mazza et al. | 435/4 |
| 4,900,513 | 2/1990 | Barker et al. | 422/64 |
| 5,289,385 | 2/1994 | Grandone | 364/497 |

Primary Examiner—James C. Housel
Assistant Examiner—Long V. Le
Attorney, Agent, or Firm—Mark J. Buonaiuto; Paul C. Flattery

[57] ABSTRACT

A sample analyzer for analyzing the characteristics of a plurality of samples. The analyzer includes a movable sample support for holding samples arranged in a first plurality of holders in a sequence for movement in a first direction. An indexing drive for the sample support advances the sample support in the first direction in a set of one or more increments, wherein one increment in the set is a net amount equal to a second plurality of holders greater than one holder and less than the first plurality such that the second plurality is relatively prime with respect to the first plurality.

20 Claims, 5 Drawing Sheets

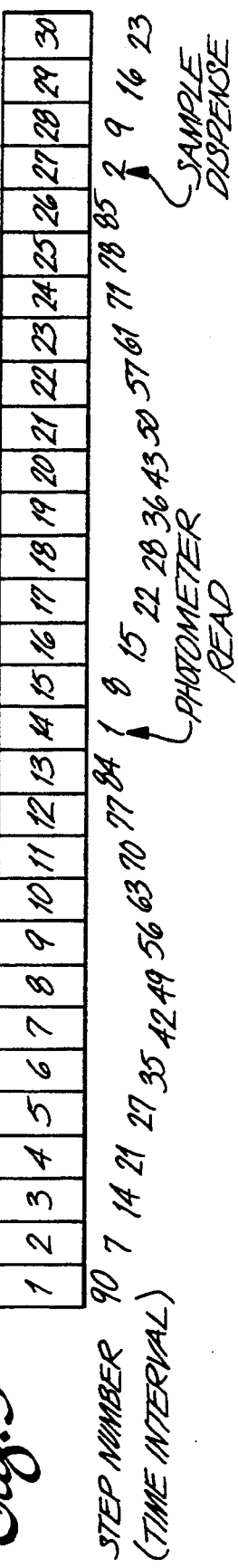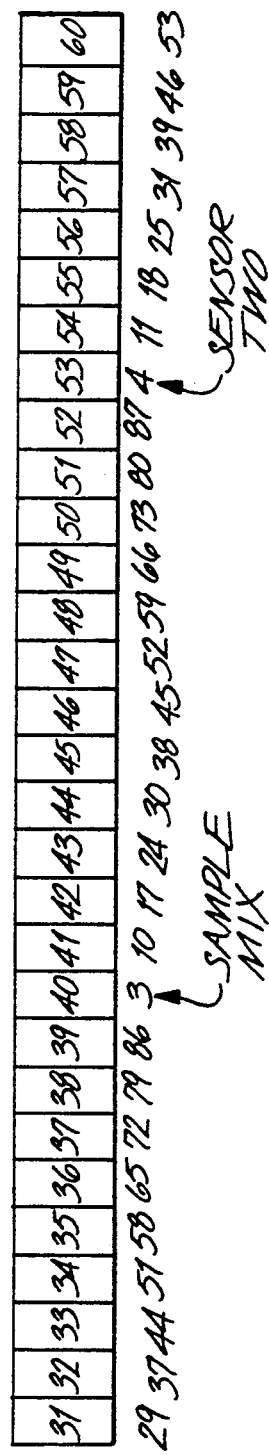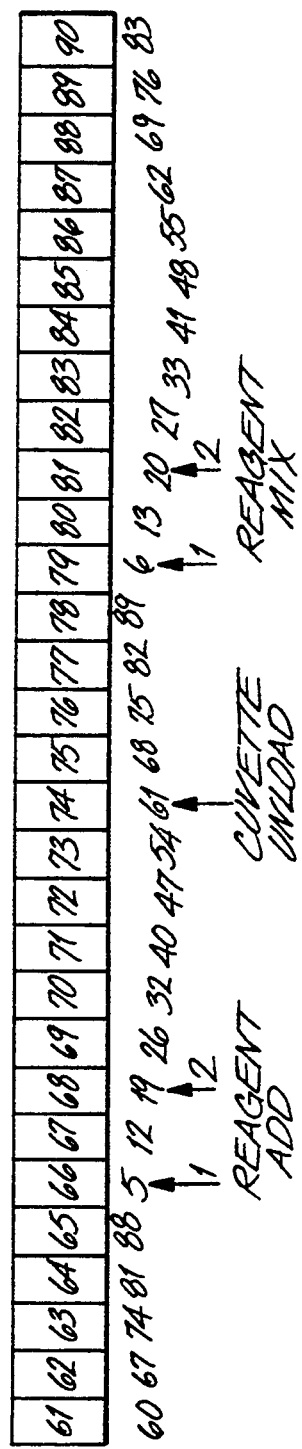
Fig. 3

Fig. 5

METHOD AND APPARATUS FOR THE STEPWISE MOVEMENT OF ITEMS

BACKGROUND OF THE INVENTION

1. Field of the Invention

The present invention relates generally to conveyor systems. The present invention has a specific application to conveyor systems for sample analyzers such as chemical analyzers for testing characteristics of bodily fluids.

2. Related Art

Automated analyzers for chemical, immunochemical and/or biological testing of samples taken from patients are well known. Chemical or physical tests are performed on biological fluids such as urine, blood serum, plasma, cerebrospinal fluid and the like. A sample of the fluid is typically combined with a prepared reagent liquid, buffer liquid and/or diluting liquid and thereafter maintained at a controlled temperature until analytical measurements can be taken, such as by a photometer. For example, the measurement process analyzes the presence in the original sample of a given biochemical substance or characteristic.

There are several types of automatic sample analyzers. Preferably, each analyzer occupies a minimum of physical space, has a high throughput, analyzes dynamic as well as completed reactions and optimizes the placement of equipment. One type of analyzer has a plurality of parallel, simultaneously operating channels, each of which is arranged to accomplish a specific analysis. The analyses may be identical, to maximize throughput, or they may be distinct, to provide a variety of tests. A second type operates in series having one single processing channel for carrying out a specific analysis. Samples are supplied in sequence and analyzed sequentially according to the specific analysis assigned to the apparatus. In both of these types of systems, physical positioning of the various processing apparatus, such as sample load units, reagent add units, reagent mix units and sample unload units, is highly constrained for small systems. Such processing apparatus must be positioned relatively closely to one another so that each apparatus can accomplish its desired function at the proper time in the testing sequence. For large analyzers, processing apparatus, which might be spaced further apart physically from one another because of spacing requirements, often are too far away from the starting point for a sample to be processed within the required reaction or sensing time. Therefore, there are both close physical constraints and time restrictions on conventional sample analyzers. Limitations created by unique analysis procedures such as for dynamic reactions also restrict analyzer design and operation. These physical and time constraints lower sample throughput and inhibit the maximum use of mechanical equipment or the number of operations available in a given time period or step.

Accordingly, there is a need for a sample analyzer and process which increases sample throughput, which permits analysis of dynamic reactions and provides for multiple scans of a given sample, maximizes the use of processing apparatus and the number of operations occurring during the process, optimizes the residence time for a given sample in the system and which analyzes a large number of samples with a single analyzer. There is also a need for a sample analyzer which disassociates physical and temporal space, e.g. which separates the logical processing steps from the physical limitations of a given system, thereby allowing discrete processing apparatus to be spaced out over the architecture of the system and so that the processing apparatus can still conform to the spacial and timing requirements for the analyzer.

It is an object, therefore, of the present invention to provide a system and apparatus for efficiently, in terms of both time and space, transporting samples or other items for processing, which provides a high throughput, which maximizes the use and positioning of processing apparatus, which maximizes the number of operations occurring in a given amount of time and which optimizes the residence times of and analysis steps for the samples or other items. It is a further object of the present invention to disassociate logical and physical space with respect to the samples or other items being analyzed and with respect to the processing apparatus, and to permit operation on a large number of samples or items with a single processing apparatus. It is also an object of the present invention to provide a sample analyzer which moves samples a plurality of times and which can perform an operation such as scanning for all samples every time the samples are moved. It is an additional object to provide a sample analyzer which can track blank sample areas for calibration or other processing.

SUMMARY OF THE INVENTION

In accordance with the present invention, an apparatus such as a sample analyzer is provided which achieves high throughput, maximizes the positioning and use of mechanical processing equipment, maximizes the number of operations on a given sample or item, and which allows analysis of a large number of items with a given piece of mechanical equipment. A sample analyzer according to the present invention analyzes the characteristics of a plurality of samples. The analyzer includes a movable sample support for holding samples arranged in a first plurality of positions for movement in a first direction. An indexing drive for the sample support moves the samples in the sample support in the first direction in a set of increments wherein each increment represents a movement of the samples an amount corresponding to a number of samples and wherein the set of increments has a number of increments constituting one or more increments. The movement of samples within all of the increments in the set of increments added together produce a sum which is a net move of the sample support an amount of samples equal to a second plurality of holders greater than one holder and less than the first plurality such that the greatest common factor between the second plurality and the first plurality is the number of increments in the set. Such a system enables separation of logical space from physical space in the system, allowing more freedom in placement of mechanical equipment while permitting proper sequencing of operations both in space and in time. Such a system can also optimize residence time for the subject items. In the context of a sample analyzer using a scanner or other sensing equipment, the sample analyzer according to the present invention allows scanning of samples with every advance or increment. Once the system and its controls are defined, the location and movement of each sample at any given time can be easily determined.

As an example of one preferred configuration which has been found to be especially convenient, the first plurality of holders constitutes 90 holders grouped in pairs. The set of increments constitutes two increments, a first increment of which includes a movement of 103 sample holders constituting a net movement of 13 sample holders, and a second increment of which constitutes a movement of 91 sample holders, constituting a net movement of one sample holder. In this configuration, the number of increments is two and the set of increments added together produce a sum of 194 which is a net movement of the sample support an amount equal to 14, which is greater than one holder and less than the first plurality 90. As a result, the Greatest Common Factor between the second plurality 14 and the first plurality 90 is 2, the number of increments in the set.

In a preferred form of the invention, the sample support is a substantially round precessor wheel which rotates about an axis in a circle for presenting a sample to a plurality of processing equipment stations. For example, a photometer may be used to scan every sample placed before it. Sample holders are grouped into 45 pairs (90 samples total) whereby the indexing drive advances or shifts the precessor wheel in pairs of rotations. The first rotation is a first increment or large rotation constituting 103 sample positions, namely a full rotation of 90 sample positions plus 13 sample positions and the second rotation is a second increment or small rotation constituting 91 sample positions, namely a complete rotation plus one sample position. In this configuration, a given sample will rotate past the photometer or other scanning instrument once each turn and returns to its original starting position after a cycle of 45 rotation pairs. Because the total net shift of 14 sample positions and the 90 positions on the precessor wheel have a greatest common factor of two, the number of increments in a set, the sample position does not return to the start position until 45 rotation pairs occurs, a first large rotation having a net increment of 13 and a second small rotation having a net increment of 1. Likewise, the same cycle occurs for every other sample position.

By rotating the precessor wheel so as to present each sample before the photometer every rotation, all samples can be read during each rotation. As a result, time dependent reactions can be continually monitored without interrupting the sequence and timing of other operations.

In a further form of the invention, a sample analyzer has a plurality of operations stations at which are positioned individual pieces of mechanical equipment, such as sensors, adding stations, mixing stations, and the like. While the stations are physically separated, they are still positioned around the precessor wheel according to the logical or temporal sequence to be followed by the samples for proper chemical analysis. Therefore, mechanical equipment need not be positioned about the sample support wheel solely as a function of when, during a ten minute reaction for example, the sample must be scanned, mixed or otherwise processed. For example, if scanning is to occur after mixing, the scanner need not necessarily by physically next to the mixer to be next in time. The sample analyzer of the present invention allows separation of logical or temporal space from physical space so that mechanical equipment can be positioned not only as a function of how much space the equipment occupies and the time that the mechanical equipment operates on a given sample, but also as a function of how often the mechanical equipment may need to be accessed, such as by service personnel.

BRIEF DESCRIPTION OF THE DRAWINGS

FIG. 3 is a schematic linear representation of an endless conveyor such as a precessor wheel depicting spatial and temporal relationships for movement of the precessor wheel in single increments of thirteen.

FIG. 5 is a schematic linear representation similar to that of FIG. 3 depicting spatial and temporal relationships for movement of the precessor wheel in pairs of increments, first a net increment of thirteen and then a net increment of one.

DETAILED DESCRIPTION OF THE PREFERRED EMBODIMENTS

According to the present invention, a sample analyzer and method of operating a sample analyzer is described which carries out processing steps corresponding to sequential, adjacent logical events or "positions" that may be physically separated, thereby maximizing use of available space and available mechanical equipment, while still allowing optimum physical arrangement of that equipment. At the same time, an optimal sample testing process is provided whereby samples are repeatedly scanned or analyzed while the sample is on the analyzer. The repeated scanning or analysis can be accomplished for a large number of samples and even using a single analyzer.

Figure 1:
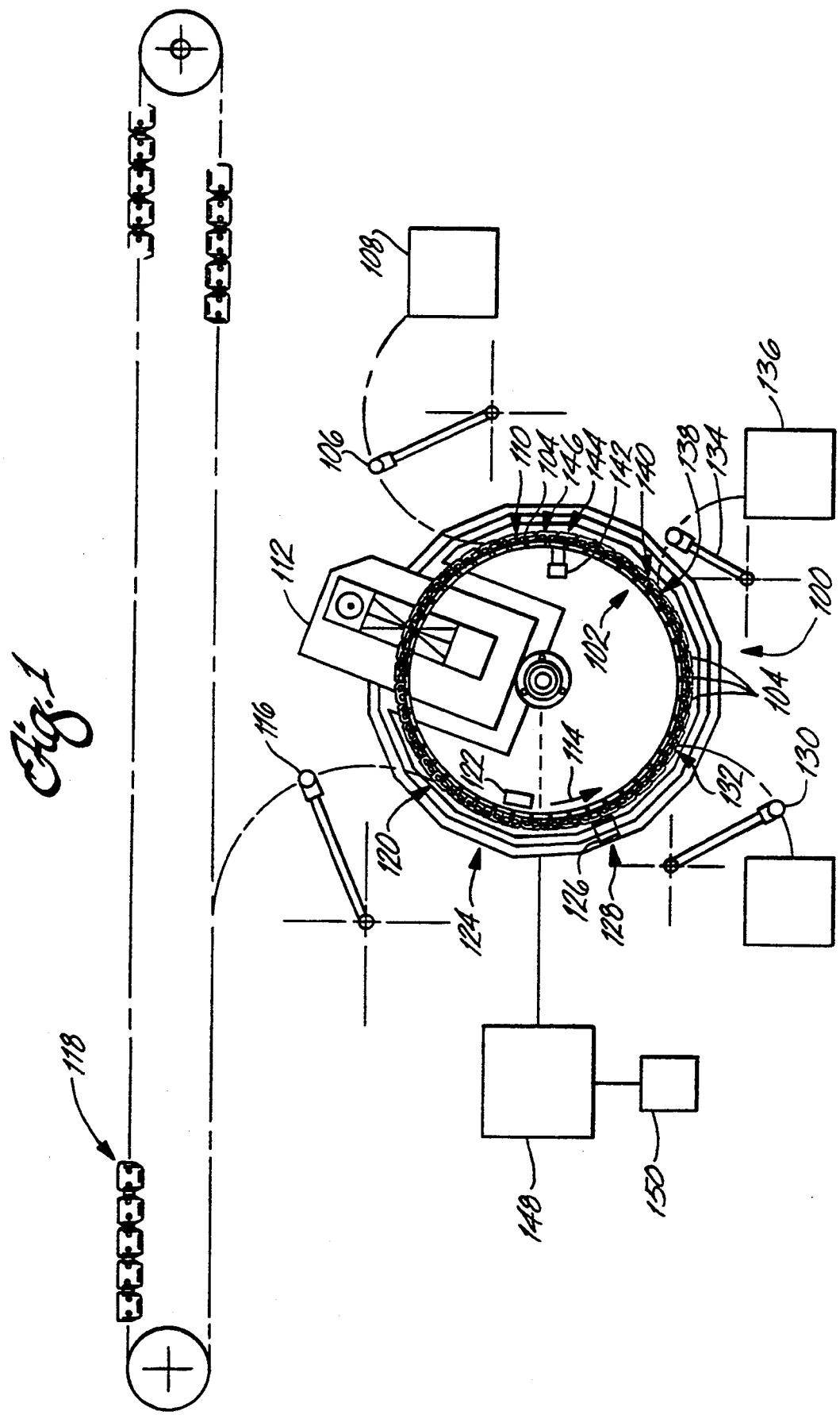
FIG. 1 is schematic plan view of a sample analyzer for use with the present invention including various equipment units which operate with the sample analyzer.

A sample analyzer 100 according to the present invention analyzes the characteristics of a plurality of samples (FIG. 1). The sample analyzer is typically the main part of an overall automated diagnostic apparatus, preferably requiring a minimum of human supervision or intervention. The sample analyzer accepts a plurality of samples, adds associated reagents and/or solutions, mixes the sample solution, measures the desired reaction or characteristic, if any, and then disposes of the sample. The optimal coordination and control of these steps, as well as the optimal positioning for carrying out these steps, is accounted for by this invention. Preferably, the coordination and control provided by this invention are applicable to a wide range of processes and configurations. The invention accounts for variations in the number of discrete operations to be carried out with respect to a specific sample, the size of the equipment being used, the space available, the desired sample throughput, the types and number of reactions or other steps to be carried out and measured, reaction times if any, and servicing requirements.

The sample analyzer 100 includes a sample support preferably in the form of an endless conveyor, such as a precessor wheel 102. The precessor wheel 102 preferably includes a first plurality of sample holders 104 for holding individual reaction vessels or sample containers to be placed into the sample holders and transported with the precessor wheel. In the preferred embodiment, each sample holder 104 preferably holds a pair of associated, discrete reaction vessels or cuvettes. Exemplary cuvettes which may be used with the analyzer such as that described herein is described in U.S. Pat. No. 4,815,978.

Cuvettes, or other containers for sample analysis, may be loaded onto the precessor wheel 102 by a cuvette load unit 106 which transports cuvettes from a cuvette supply and preparation unit 108 to an empty sample holder on the precessor wheel when the precessor wheel presents an empty holder at the cuvette load station 110. The cuvette load station 110 is one of a plurality of stations at which each sample holder on the precessor wheel will be presented on a cyclical basis. Each cuvette, or in the preferred embodiment each cuvette in a linked pair of cuvettes, will be presented to a number of other discrete stations at which various equipment is positioned for carrying out specific operations on each cuvette positioned before it. While there are a number of equipment units that can be used with the sample analyzer of the present invention, the equipment units discussed in conjunction with the present invention include a photometer, sample dispense unit, a sample mix unit, an ISE instrument (ion sensitive electrode), a reagent add unit and a reagent mix unit. However, any other suitable equipment may also be used. Each piece of equipment is positioned at a respective station oriented at selected locations about the precessor wheel.

While it is possible that the precessor wheel can be rotated so that each cuvette is advanced around a circle one cuvette position at a time, such a sequencing process would require much of the equipment units used with the sample analyzer to be positioned very close to the sample load station 110 in order to accomplish necessary operations within the required time interval. Because of the time dependent nature of many sample reactions, many of the processes carried out by the other discrete equipment units must be carried out relatively close in time to one another. Using stepwise advances of the precessor wheel to move each cuvette one position with each movement would require the discrete equipment units to be physically positioned close together so that the associated processes can be carried out close in time. Significantly, the present invention allows the various equipment units to be separated spacially relative to one another about the precessor wheel while still permitting their associated operations to occur close in time. Therefore, the present invention permits disassociation of logical and temporal space in terms of the system operation and timing requirements from the physical space, in terms of not only positioning of discrete equipment units, but also in optimizing the number of samples that can be handled on the precessor wheel, locating equipment units for such considerations as service requirements, and for optimum use of individual equipment units.

The cuvettes loaded at the load station 110 may be empty, dry cuvettes or may include solutions, reagents or other materials already added to the cuvette prior to loading on the precessor wheel. Any number of steps can be accomplished in the cuvette supply and preparation unit 108 or preliminary thereto as would be known to those skilled in the art. The cuvette supply and preparation unit 108 may take the form of any number of apparatus for separately or in combination preparing a cuvette for loading on the precessor wheel.

Additional equipment used for carrying out the sample analysis is distributed about the precessor wheel at such locations as to permit the necessary operations within the time constraints dictated by the possible reactions and analyses carried out by the sample analyzer and also according to spatial constraints. A sensor such as a short duration pulse photometer 112 is preferably placed at a first station 113 downstream from the cuvette load station 110 so that the first operation conducted on the cuvette just loaded is a photometer scan of the cuvette and its contents, after the precessor wheel moves in a first counterclockwise direction as indicated by arrow 114, and before sample solution or other reagent is added to the cuvette. The photometer also scans each cuvette as it passes, as described more fully below.

In the preferred embodiment, a sample dispensing unit 116 obtains sample from a sample delivery assembly 118 and adds a sample portion to an individual cuvette presented at a sample dispensing station 120. The sample dispensing unit 116 is shown schematically in FIG. 1, but it should be understood that the sample dispensing unit can take one of many forms known to those skilled in the art. Aliquots of sample can be taken from containers held in the sample delivery assembly 118 and transferred directly to a cuvette assigned to accept the sample portion, or the sample dispensing unit 116 can physically remove the sample container from the sample delivery assembly and thereafter transfer a portion of the sample from the container to the cuvette.

A sample mix unit 122 is preferably positioned at a sample mix station 124 downstream from the sample dispensing station 120 to mix the sample portion just added to the cuvette with any material that was already present in the cuvette. The sample mix unit may be any well known unit used for that purpose.

A cuvette unload unit 126 is preferably located downstream from the sample mix unit 122 for removing a cuvette pair from its associated sample holder when the cuvette pair is presented at the cuvette unload station 128. Preferably, each cuvette is sealed before it is disposed of in an appropriate container or other disposal unit. As will be apparent from the discussion below, the cuvette unload unit is not the next unit which operates on the cuvette immediately after the cuvette leaves the mixing unit 122. The cuvette unload unit 126 is positioned apart from the sample delivery assembly 118 and the cuvette load station 110 so that the container of unloaded cuvette pairs can be easily accessed by technicians. However, even though the cuvette unload unit 126 is adjacent the sample mix unit 122, the operations carried out by those two units on the same cuvette occur temporally far apart from each other. With the method and apparatus of the present invention, the cuvette unload unit 126 can be placed at a number of physical locations about the precessor wheel and still unload cuvettes from the precessor wheel near the end of a given cycle, a cycle beginning when a particular cuvette is loaded in a sample holder and ending when the same sample holder, now empty, returns to the same position for loading of a new cuvette.

An ISE aspiration unit 130 is placed downstream from the cuvette unload unit for conducting further operations on individual cuvettes placed before it when the precessor wheel stops. The ISE aspiration unit is an ion sensitive electrode available from Baxter Healthcare for determining characteristics of a solution, such as the solution in a cuvette. In the preferred embodiment, a given cuvette which has just finished being mixed by the mixing unit 122 is next presented to the ISE aspiration unit 130 at the ISE station 132. Even though the ISE unit 130 is physically adjacent the cuvette unload unit 126, the controlled sequence of operations on a given cuvette places the cuvette at the ISE station 132 after the cuvette leaves the mix station 124 and before the same cuvette is presented before the unload unit 126. As will be apparent below, in the preferred form of the invention, a given cuvette is presented first to the photometer 112 after it is loaded on the precessor wheel, and then presented to the sample dispensing unit 116, the sample mix unit 122 and then the ISE unit 130.

A reagent add unit 134 is positioned physically downstream from the ISE unit 130 for adding reagents, if necessary, to cuvettes presented at a reagent add station (138, 140). The reagent add unit 134 takes reagent from a reagent supply 136 to be added, if necessary, to a cuvette presented at a first reagent add station 138. The same or different reagents may be added, if necessary, to cuvettes presented at a second reagent add station 140 either by an additional reagent add unit or by the first reagent add unit 134 with appropriate modification of the unit. As will become apparent below, a single reagent add unit can be used to add reagent to the cuvette at add station 138 and can also be used to add reagent to reagent add station 140. The reagent add stations 138 and 140 are physically adjacent, but also are temporally far apart, because the cuvette at station 138 is not shifted in the very next step to the immediately adjacent cuvette position at station 140. Therefore, a single reagent add unit can cover two stations rather than only one.

A reagent mix unit 142 is positioned physically downstream from the reagent add unit 134 and before the cuvette load station 110. The reagent mix unit 142 can operate on a cuvette presented at the first reagent mix station 144 and can also operate on a second reagent mix station 146. The reagent mix unit 142 may be a conventional device as known to those skilled in the art.

The sample analyzer further includes an indexing drive 148 for rotating the precessor wheel 102 preferably in the first direction 114 in a set of one or more increments. The increments are used to advance a given cuvette, according to the preferred time schedule, and present the given cuvette before the appropriate stations to allow the units at each station to accomplish their respective operations as to that cuvette. The indexing drive 148 is controlled by a control unit 150 according to software, firmware or hardware commands or circuits to advance the precessor wheel according to the preferred set of increments.

An increment is an amount by which the precessor wheel is advanced. The increment is defined in terms of a single cuvette holder, or its equivalent, such as degrees of arc for the precessor wheel. Therefore, in the preferred embodiment where the precessor wheel includes 90 cuvette holders, or 45 pairs of cuvette holders, an increment of one cuvette holder is that amount of precessor wheel movement necessary to move a single cuvette holder from a current position to the next adjacent single cuvette position in the counterclockwise direction. It should also be understood that an increment constituting a net amount of one cuvette holder could also include a precessor wheel movement of exactly 360° plus an amount equal to one cuvette holder, in other words a total of 91 cuvette holder positions in one preferred embodiment. The end result in either case is to advance, shift or increment the given cuvette holder an amount of one cuvette holder position.

In a preferred embodiment of the invention, the cuvette holders on the precessor wheel are shifted in a first direction in a set of increments wherein each increment represents a movement of the cuvettes an amount corresponding to a number of samples. Specifically, there are two increments in the set of increments and the first increment represents a movement of the cuvettes an amount corresponding to 103 cuvettes and the second increment constitutes a movement of the cuvettes an amount corresponding to 91 cuvettes. The movement of the cuvettes with the two increments in the set of increments added together produce a sum of 194 which constitutes a net move of the precessor wheel 14 cuvettes. The 14 cuvettes is greater than one cuvette and less than the 90 cuvettes and the greatest common factor between the 14 cuvettes and the 90 cuvettes is 2, the number of increments in the set. The control unit 150 controls the indexing drive 148 to advance the precessor wheel 102 a first net amount of 13 holders and then a second net amount of 1 holder. The net amount of 14 holders is greater than one holder, and it is also less than the first plurality of 90 holders. A net increment of 14 holders with 2 increments in a set, one 13 and the other 1, will place each cuvette at each of the 90 cuvette positions once at some point during the cycle, without duplication because the greatest common factor between 14 and 90 is 2. The net total increment of 14 holders also returns a given cuvette holder to the cuvette load station after 90 precessor wheel rotations or 45 pairs.

In the preferred embodiment, an increment includes 90 sample holders plus one or more sample holders so that every shift of the precessor wheel 102 is greater than 360 degrees. This preferred increment allows the photometer 112 to scan each individual cuvette as the cuvette passes the photometer station 113. Therefore, even though the net amount of shift is less than 90, the control unit 150 controls the indexing drive 148 to advance the precessor wheel a full 90 sample holder positions plus a net amount, preferably equal to 14. By scanning all cuvettes which are present in sample holders, and any empty sample holders which have yet to be loaded, dynamic reactions can be regularly monitored. Repeated scanning with the photometer also provides for scanning a wide variety of reactions even though the reactions go to completion at different rates. Scanning empty sample holders provides a control quantity. Therefore, repeated scanning tied to every shift of the precessor wheel ensures proper scanning of a wide variety of reactions.

In the preferred embodiment, the control unit 150 provides control signals to the indexing drive 148 according to a variation on the following modulo arithmetic relationship:

$$R = I \bmod M; \tag{1}$$

where $I$ = the increment or shift by which the precessor moves; (2)

$M$ = the total number of positions on the precessor wheel; and (3)

$R$ = the number of positions remaining after the number of positions M is divided into the increment I. (4)

As can easily be shown using the theory of modular arithmetic, if I and M are relatively prime, that is, they have no common factors other than one, the precessor wheel will be indexed by the indexing drive M times in a cycle before a given sample holder will return to its original position from which it started at the cycle start. The relationship also shows that before the sample holder returns to its starting position, the sample holder will stop at all the positions corresponding to the other 89 sample holder positions on the precessor wheel. Therefore, with this relationship, for M=90 it will take 90 shifts for a given sample holder to return to its starting position and every sample holder will be presented at every discrete location about the circumference of the precessor wheel once before the cycle ends. If the greatest common factor of M and I is k, the wheel will return to its starting position after M/k shifts of I positions. Therefore, equipment can be placed around the circumference of the precessor wheel since every sample holder will stop once and only once in a given cycle of 90 shifts at any given position.

At this point, the only undetermined parameter is the precise time at which a given sample holder will be presented to a particular position around the circumference of the precessor wheel. This time element depends first on the amount of the shift forward, "I", the time interval required for each shift forward and the time delay between the end of one shift forward and the beginning of the next subsequent shift forward. As an example, disregarding for the moment the time interval for each shift forward and the delay, a net shift forward of one sample holder means that the sample holder will arrive at a position which is physically close to the starting position in a relatively short amount of time. Likewise, a position which is far away from the initial starting position would mean the sample holder would take a commensurately longer time to arrive at that position with net shifts of only one sample holder. Conversely, a larger shift forward, for example a first net amount of 13 sample holders puts the sample holder position 13 relatively close in time. Sample holder position 26 is the next closest and so on. Therefore, for a 13 sample holder net shift, an operation which would need to be done fairly soon after the sample is placed in the precessor wheel at sample holder position 1 could be placed at sample holder position 14.

The foregoing example assumes only one size of increment in the cycle. Equation (1) can be generalized for situations where the precessor wheel rotates through a pair of increments, or through any set of increments greater than one. A plurality of increments are useful, for example, where the cuvettes are associated in cuvette pairs, such as where two cuvettes are linked by a physical web for ease of handling, and where each operation on one cuvette is preferably next carried out on the associated cuvette. If the sequence of operations were otherwise, the difficulty of handling the second cuvette and its associated operations is compounded, and may make for an inefficient system. Therefore, a relationship applicable to a set of increments having more than one increment is the following:

$$GCF(S_{tot}, M) = n \quad (5)$$

where
GCF means Greatest Common Factor;

$$n = \text{number of cuvette positions in a group;} \quad (6)$$

$$S_{tot} = S' + \text{Sum over } j \text{ of } S_j'' \text{ (namely, the net primary position shift plus the net of the sum of all secondary position shifts)} \quad (7)$$

$$M = g \cdot n; \quad (8)$$

$$g = \text{number of "groups" of cuvettes on the wheel.} \quad (9)$$

A primary shift is here defined as a net shift of the wheel from one group of samples to another, whereas a secondary shift is a net shift of the wheel that ends up at a new position still within the same group. M is the total number of assigned wheel positions.

In a preferred embodiment of the invention, S total is a net shift of 14 cuvette positions constituted by a net primary position shift S' of 13 plus the net sum of all secondary position shifts $S_j'$, namely a single net increment of 1, resulting in an S total of 14. The value of M is 90 so that the greatest common factor between 14 and 90 is "n" or 2. Specifically, the number of increments in the set of increments, "n", equals 2 which in the preferred embodiment is determined by the number of cuvettes associated with one another, namely 2 as determined by a cuvette pair. The relationship in Equation (8) is also satisfied since M is 90, the number of "groups", or "g", of cuvettes on the wheel is 44 and "n" equals 2, the number of cuvette positions in a group.

With the foregoing relationships, the indexing drive 148 is controlled by signals from the control 150 so as to turn the precessor wheel according to the following general sequence:

1. Position precessor wheel to sample holder position 1 (start)
2. rotate S' (primary shift to new group)
3. Perform operation
4. J=1
5. While j is less than s,
6. rotate precessor wheel an amount $S_j$ (secondary shifting within the current group)
7. Perform operation;
8. j=j+1
9. End j
10. Go to line 2.

Figure 2:
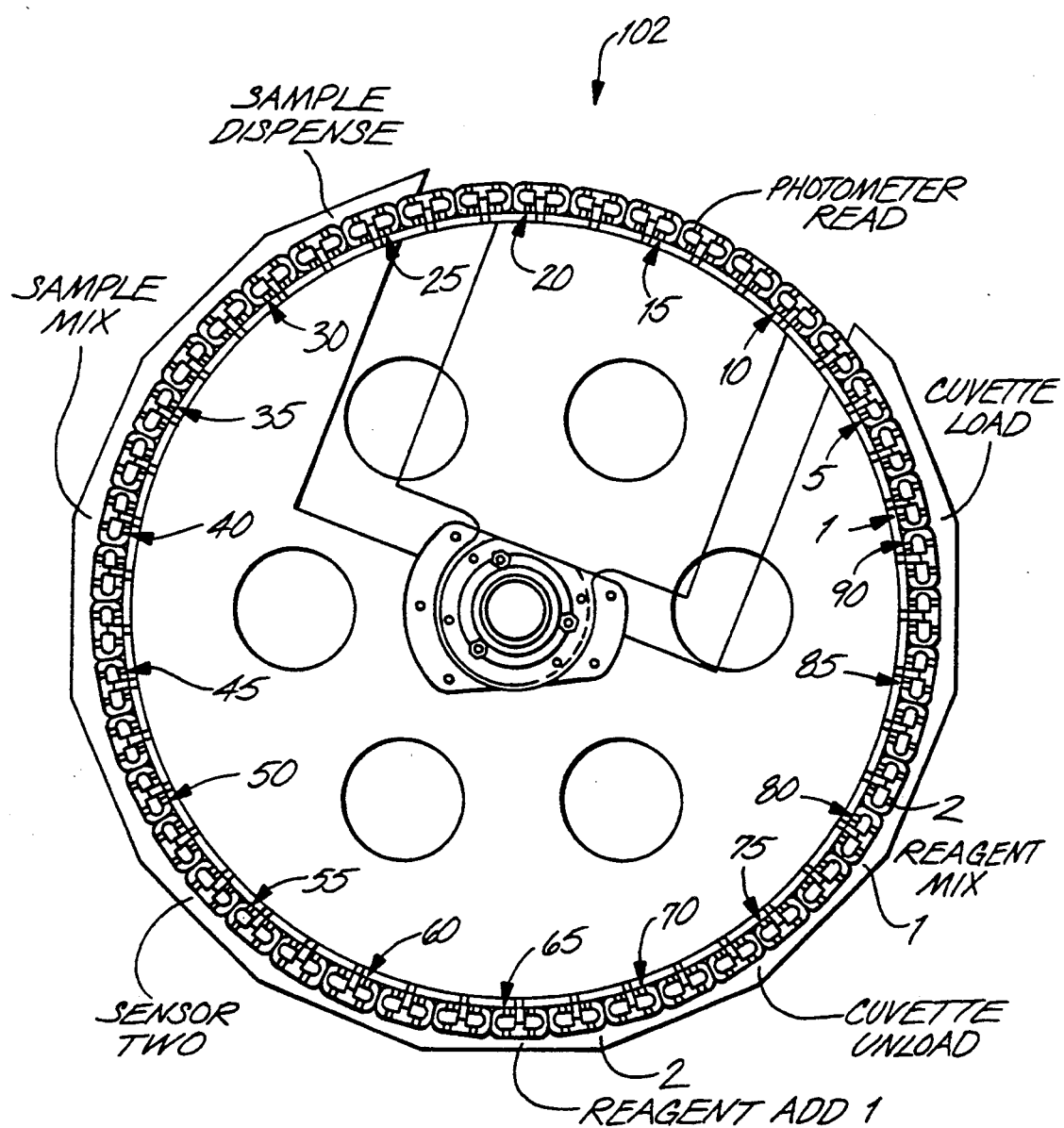
FIG. 2 is a plan view of the sample analyzer according to one aspect of the present invention showing a movable precessor wheel and a plurality of sample holders.

To illustrate the spatial and temporal relationships defined by these relationships, an example for n=1 will be discussed, followed by a discussion of an example where n=2. A precessor wheel 102 (FIG. 2) has been shown at rest in a starting configuration with every fifth sample holder position numbered, namely 5, 10, 15, etc. The numbering system corresponds to physical sample holder positions relative to other stationary equipment, such that if a cuvette placed in sample holder position 1 is shifted by rotation of the precessor wheel, "sample holder position 1" will still be as shown in FIG. 2 even though the physical sample or cuvette originally occupying that position has shifted counterclockwise. Specifically, the sample holder position numbers remain stationary even if the precessor wheel moves. For purposes of understanding and easier illustration, the sample holder positions for the precessor wheel have been separated into three 30-segment linear rows (FIG. 3) with the sample holder position numbers entered in the boxes. While FIG. 3 is a linear depiction of the sample holder positions, it should be understood that FIG. 3 is a linear representation of the continuous conveyor endless system shown in FIG. 2.

In order to determine suitable locations for equipment units, it is assumed that an individual sample cuvette is first loaded into sample holder position "1". Various equipment units will carry out respective operations on cuvettes as the cuvettes are presented before each equipment unit. For "M" equals 90, an increment or shift forward of "103" can be selected. The shift forward of "103" results in a net advance of 13. The Greatest Common Factor between 13 and 90 is 1. The reasons for selecting a net shift equal to 13 will become apparent in conjunction with the discussion below of the preferred embodiment relative to FIGS. 4 and 5. While it should be understood that the preferred shift or advance equals "103", only the net shift of 13 will be used for clarity. With a first cuvette loaded in sample holder position "1", the first net shift of 13 sample holder positions places the cuvette at sample holder position "14" (FIG. 3). After the second net shift of 13, the cuvette is presented at sample holder position "27". Each net shift is identified by a step number, and these step numbers are mapped onto the corresponding positions shown in FIG. 3. Because each cycle takes 90 rotations to complete and return the cuvette holder to its start position, there will be 90 steps and 90 step numbers. As will be discussed more fully below with respect to the preferred embodiment, the step number also represents a time interval. Assuming the precessor wheel revolution time for a shift of "103" and the precessor wheel stop time are constant, the step number also represents the time elapsed from the start with respect to the first cuvette.

As shown in FIG. 3, the positions taken by the first cuvette after each of the first six shifts are ,relatively evenly distributed about the circumference of the precessor wheel. Therefore, in a hypothetical situation where there are six equipment units, all six can be evenly distributed around the circumference of the precessor wheel and still have the first cuvette placed before all six stations in the first six time intervals. Additionally, if it is found that all reactions are completed after 60 time intervals, the cuvette unload station can be placed at a cuvette holder position corresponding to any of the time intervals between time intervals or step numbers 61 and 89. For example, a suitable spatial position for a cuvette unload station could be sample holder position 74, which is five cuvette positions apart from sample holder position 79 which may have the sixth equipment unit. Therefore, while the sample unload unit may be physically close to the sixth equipment unit, they are greatly separated in time.

Hypothetical equipment units have been positioned about the precessor wheel so that six units, namely photometer read, sample dispense, sample mix, sensor two, reagent add and reagent mix, are relatively evenly distributed spatially about the circumference of the precessor wheel. These units have been placed so that the first cuvette is presented before each of the six units in the first six steps or increments out of a total of 90 steps. Such an arrangement separates the logical sequence of cuvette movement from the physical positioning of a cuvette on the precessor wheel. It also permits optimum physical placement of the equipment units and optimum placement of such units as a cuvette unload unit at any desired location around the precessor wheel which the cuvette will visit near the temporal end of its cycle of 90 position shifts. Therefore, assuming sample holder position numbers 55 through 75 are at the front of the sample analyzer apparatus and the cuvette unload unit is placed at position 74, the cuvette unload unit is easily accessible for service.

Another beneficial feature of the invention can be seen by considering the reagent add and reagent mix units depicted in FIGS. 2 and 3. With a reagent add unit which can access two different locations relative to the sample holder positions on the precessor wheel, such as sample holder positions 66 and 68, a single reagent add unit can be used to perform operations on the sample cuvette when it is presented at position 66 as well as when it is presented later at position 68. Since the cuvette in this example is presented at position 66 at the fifth step number, or after the fifth time interval, and the same cuvette is presented at position 68 after the 19th time interval, the reagent add unit has sufficient time after operating at position 66 to prepare for performing an operation at position 68. Specifically, the reagent add unit has approximately 14 time units to prepare for the first cuvette to arrive at position 68. As a result, a single equipment unit can be located at one physical position relative to the precessor wheel and make two or more operations which occur at different times. The same comments apply to the reagent mix unit or other equipment units which may be used. Conversely, operations which are intended to occur close in time can be spaced far apart. For example, the sample dispense operation occurring at sample holder position number 27 occurs only two time units before the sample is analyzed at sensor two at sample holder position number 53. Such spatial separation permits optimum positioning of equipment units and efficient use of space about the precessor wheel. Therefore, physical location and temporal location are disassociated.

With a shift or advance of "103", each cuvette will pass the photometer read station within the span of each shift or time interval. As a result, the photometer unit can monitor dynamic reactions in every cuvette, starting with the first shift after sample is dispensed at the sample dispense unit at sample position holder position 27. The reaction in each cuvette is thereafter monitored with each precessor wheel shift until the cuvette is unloaded at sample holder position 74.

The wide spatial separation of equipment units permits a relatively large number of samples to be maintained on the precessor wheel at any given time. This provides a significantly high throughput of samples in the sample analyzer. It also maximizes the number of operations occurring with each step since mechanical equipment can be positioned as desired around the circumference of the precessor wheel using a format such as depicted in FIG. 3. Once the relationships shown in FIG. 3 are defined, and the time intervals are determined, every operation and the location of every sample at any given time is known.

Figure 4:
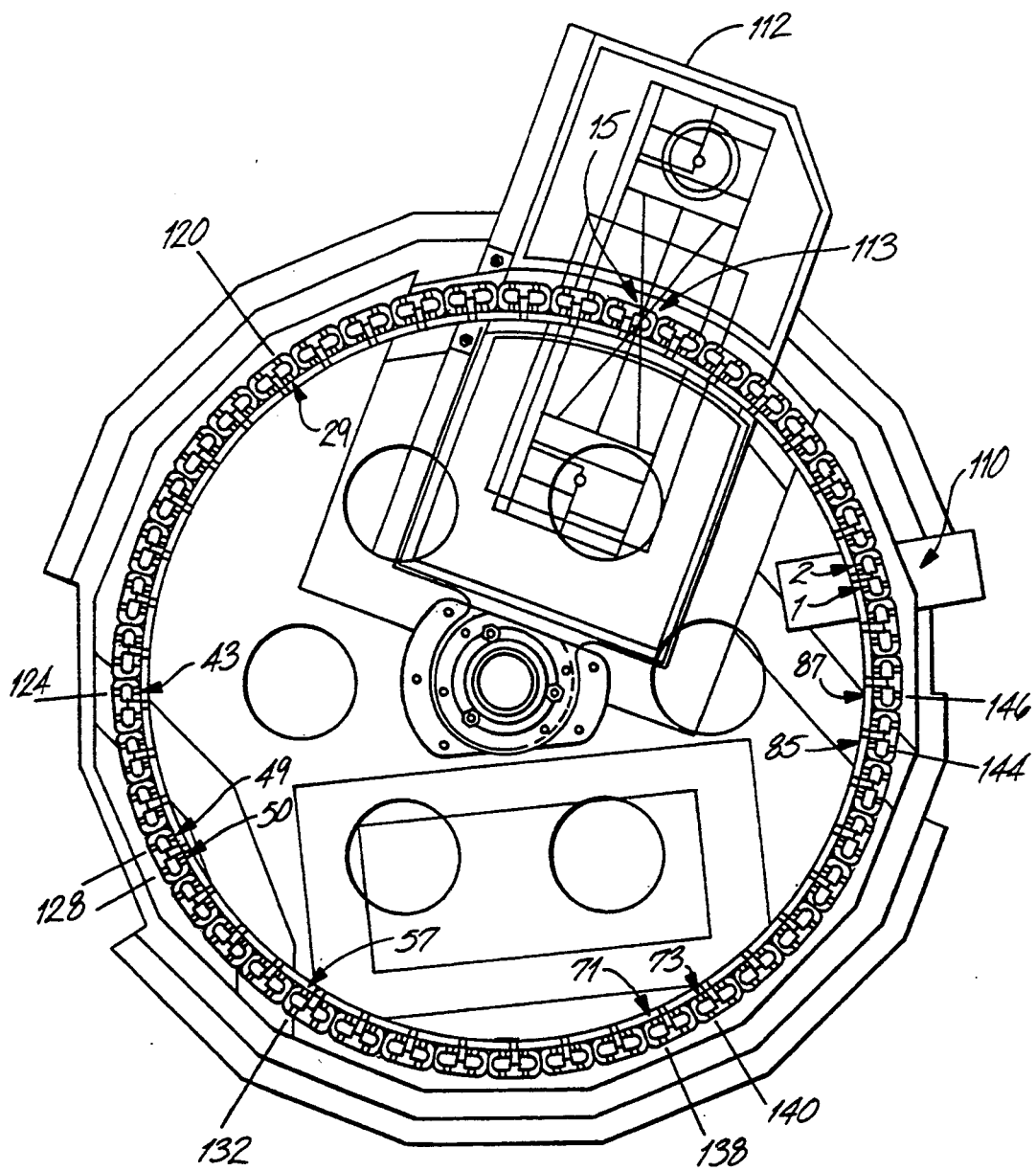
FIG. 4 is a plan view of the precessor wheel of FIG. 1 and depicting equipment stations.
Figure 5:
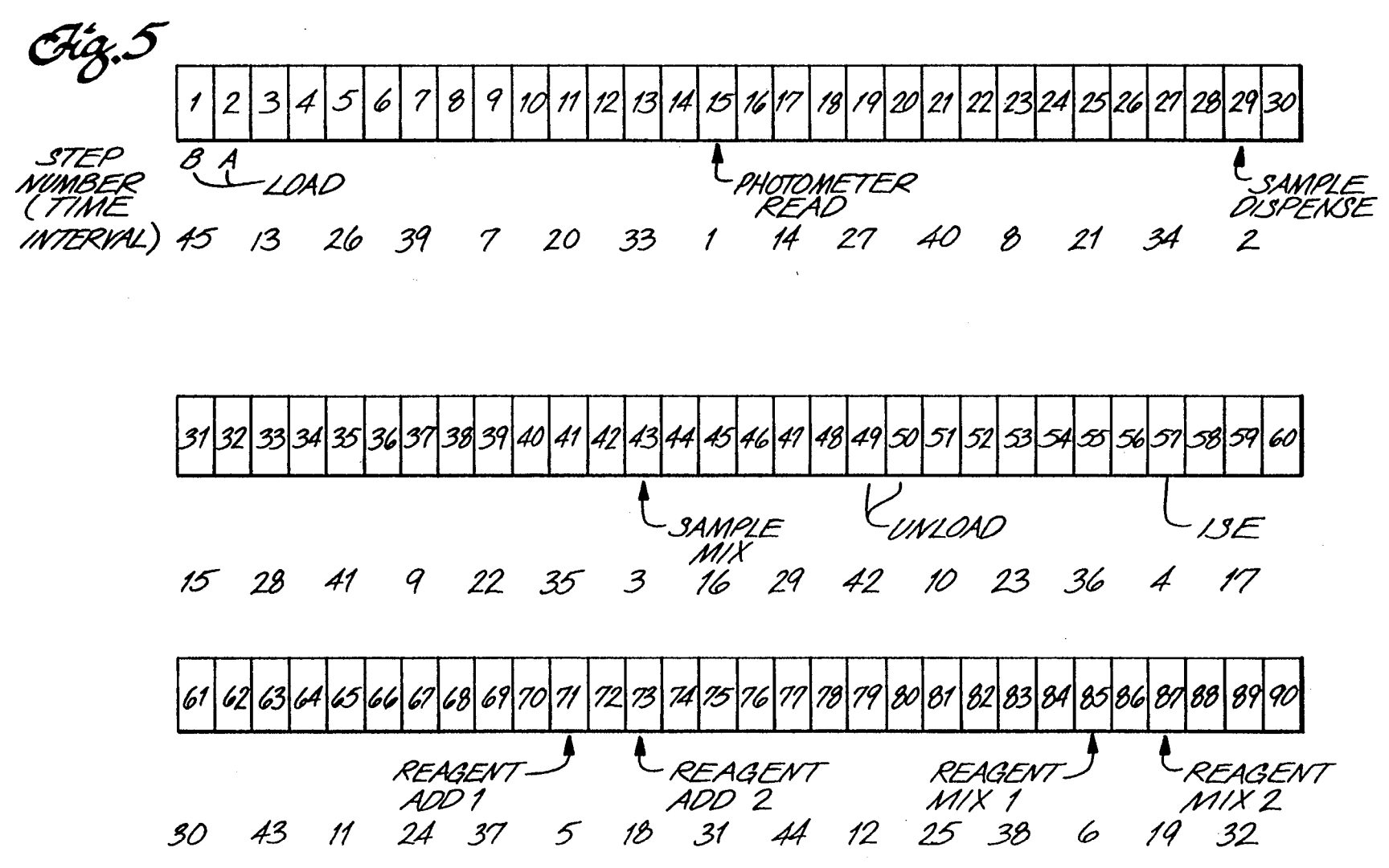

In a preferred embodiment, sample cuvettes are handled in pairs wherein two cuvettes are connected by a web. The cuvette pair is then loaded onto the precessor wheel at the cuvette load station 110 so that the forward or "A" cuvette is in sample holder position 2 and the following cuvette "B" is in sample holder position 1 (FIGS. 4 and 5). While it is clear that handling of the sample and reagent in cuvette "A" can be handled expeditiously under the scheme discussed above with respect to FIGS. 2 and 3, the second cuvette "B" of the pair is not accounted for. Therefore, treatment of the second cuvette "B" is preferably tied to the processing of cuvette "A".

In the preferred embodiment, the precessor wheel shifts a set of two increments for each cuvette pair. The quantity "n" is 2. The first increment in the set shifts cuvette "A" to present the cuvette before a particular equipment unit, after which the precessor wheel moves the second increment in the set to present the second cuvette "B" before the same equipment unit. Therefore, the same equipment unit processes first the cuvette "A", and immediately thereafter the second cuvette "B" so that each cuvette of the pair visits the same precessor position one after the other. This avoids having two photometer units, one for each cuvette in the pair, as well as dual equipment units at other equipment stations. Therefore, in the preferred embodiment, after a cuvette pair is loaded at the cuvette, load station 110, the precessor wheel rotates an increment or large rotations of 103 sample holder positions, resulting in a net shift of 13 sample holder positions to place the first cuvette "A" at sample holder position 15, the photometer station 113. After the cuvette "A" stops and is scanned by the photometer 112, the precessor wheel rotates a second increment or small rotation of 91 sample holder units to present the second cuvette "B" at the photometer station 113 to be scanned. The net shift for the large and small rotations $S_{tot}$ is 14 sample holder units. The precessor wheel then undergoes a second set of large and small rotations to sequentially present the first and second cuvettes before the sample dispense station 120 at sample holder position 29. A third set of large and small rotations brings the first and second cuvettes sequentially before the sample mix station 124 at sample holder position 43. A fourth set of large and small rotations bring the first and second cuvettes before the ISE station 132 at sample holder position 57. The first and second cuvettes are then presented to reagent add 1 station 138 at sample holder position 71 after a fifth set of large and small rotations, after which the first and second cuvettes are presented to reagent mix 1 station 144 at sample holder position 85. In the preferred embodiment, each cuvette in the precessor wheel, including the first and second cuvettes "A" and "B" are scanned during each large and small rotation, since each shift is at least 90 sample holder positions. Each cuvette is scanned by the photometer 112 as the precessor wheel rotates.

As shown in FIG. 5, after 18 steps, the first and second cuvettes are presented before the reagent add 2 station 140 at sample holder position 73, and thereafter presented to reagent mix 2 station 146 at sample holder position 87. After 42 sets of large and small rotations, the cuvette pair is presented at the cuvette unload position 128, in sample holder positions 49 and 50 to be sealed and unloaded from the precessor wheel. The sample holders corresponding to the removed cuvettes remain empty for the remaining three sets of large and small rotations until the pair of sample holders are again presented before the cuvette load station 110 after the 45th set of large and small rotations. In the preferred embodiment, the photometer 112 scans the empty sample holders on each large and small rotation after the cuvette pair are unloaded as a calibration and system check.

It should be noted that the step numbers shown in FIG. 5 correspond to each set or pair of large and small rotations. Therefore, the sample holder corresponding to the first and second cuvettes returns to the cuvette load station 110 after 45 sets or pairs of large and small rotations. Only the first large rotation of each set is depicted by the step numbers in FIG. 5. Each small rotation in the set advances the cuvette one sample holder position. For example, the first cuvette "A" is shifted in a large rotation to sample holder position 15. After the small rotation of 91, the first cuvette "A" is located at sample holder position 16 while the second cuvette "B" is positioned at the photometer read position corresponding to sample holder position 15. Subsequent sets of large and small rotations result in similar shifts.

In the preferred embodiment depicted in FIGS. 4 and 5, equations 1–7 are satisfied where the number of positions "M" is 90, the increment or shift advance "I" is 103 for the large rotation, "n" is 2 and the number of increments in a set is 2. The quantity $S_{tot}$ equals 14, the sum of the net primary position shift S' of 13 and the net of the sum of the single secondary position shift equal to 1. The number "g" is 45 groups of cuvettes on the wheel and "n" equals 2 such that Equation (8) is satisfied. Therefore, the Greatest Common Factor between $S_{tot}$ (14) and M (90) is 2. These values are then used to operate the indexing drive according to the general process described above. The process using these values will now be demonstrated.

After the cuvette pair is added at the cuvette load station 110, following a small rotation of 91 to place the first and second cuvettes as shown in FIG. 4, the precessor wheel rotates a first rotation "S'", corresponding to a net advance of 13. The photometer 112 then scans the first cuvette "A" at the photometer station 113. Then, while "j" equals 1, which is less than n=2, the precessor wheel rotates a small rotation of 91 corresponding to "$S_j$", after which the second cuvette "B" is scanned by the photometer 112. The index "j" is incremented to be equal to "j" plus 1, making "j" no longer less than n. The process then returns to step 2, where the wheel then makes a large rotation "S'" and the process continues. It should be noted that this process can be carried out with triplets of linked cuvettes and any number of cuvettes where Equation (8) is satisfied. It should also be noted that the large rotation can have a net shift other than 13 as long as the Greatest Common Factor of $S_{tot}$ and "M" is "n".

The relationship of Equation (5) provides a number of benefits. In the particular embodiment disclosed in FIGS. 4 and 5, a net shift on the first large rotation of 13 sample holder positions allows the photometer to be spaced apart from the cuvette load unit. It also permits the first operation for the newly loaded cuvette to be a photometer scan to give a standard or calibration measurement for the cuvette. The second, small rotation of 91 sample holder positions takes care of the second of the pair of cuvettes loaded at the cuvette load position 110. These net shifts of the precessor wheel also allow the other equipment units to be spaced apart around the circumference of the precessor wheel but still have the sample dispense operation, the sample mix operation, the ISE operation, the reagent add 1 and reagent mix 1 operations occurring sequentially in a relatively short amount of time. However, because each cuvette will be presented in subsequent rotations to the same general arcuate area or sector as each of these six equipment units, these equipment units can be positioned to perform an operation on the cuvette at almost any selected step or time interval during the cycle for which the particular cuvette is on the precessor wheel. Therefore, the unload unit 126 can be placed just about anywhere on the precessor wheel within the constraints defined by the spacial restrictions of the other equipment and the necessity for servicing the equipment at the unload station 128. Moreover, because each cuvette will revisit a given sector on the precessor wheel at a number of different times over the cycle, a given equipment unit can be designed to operate at different times on different but relatively close sample holder positions. For example, the reagent add and reagent mix units preferably can operate on sample holder positions 71 and 73 and sample holder positions 85 and 87, respectively (FIG. 5). Therefore, logical and temporal space can be separated from physical space. This also maximizes the use of the equipment units. Additionally, by spacing the equipment units around the circumference of the precessor wheel, the number of operations occurring with each shift can be maximized.

As shown in FIG. 5, a cuvette pair is unloaded from sample holder positions 49 and 50 after the 42nd step or pair of rotations is completed. During the next subsequent rotation, there are six vacant sample holders which are scanned by the photometer 112 to provide a baseline, standard or calibration measurement. A given pair of sample holder positions remain vacant for three pairs of large and small rotations before a new cuvette pair is loaded after the 45th rotation pair.

Each rotation pair generally results in a new cuvette pair being loaded at the cuvette load station 110. For example, after the first and second cuvettes "A" and "B" are shifted to sample holder positions 15 and 14, respectively, the vacant sample holder which was at sample holder positions 77 and 78 are shifted after a large rotation first to sample holder positions 90 and 1, and then after a small rotation to positions 1 and 2. Therefore, after the small rotation and while cuvette "B" is being read at the photometer station 113, a new cuvette pair is being loaded at the load station 110. This second cuvette pair then follows the same procedure as described above with respect to cuvettes "A" and "B". The process continues as long as there is demand for sample analyses. However, sample analyzers can be programmed as is known to those skilled in the art to discontinue loading cuvettes if there is no demand.

In the preferred embodiment, the first plurality of sample holders "M" is preferably 90. A total of 90 sample holder positions provides a relatively large number of positions for the desirable sample throughput for the sample analyzer. Additionally, given the rotation parameters and size of the precessor wheel for 90 holders, the apparatus and the method for carrying out the shifts provides an assembly which completes a cycle in approximately the same time that it takes for the anticipated longest reaction to occur. Ninety positions also permits a suitable number of shifts or advances of the precessor wheel, namely six for the preferred embodiment, before a given cuvette pair returns to the same general area or sector from which it started. For example, the first cuvette pair stops at sample holder positions 15, 29, 43, 57, 71 and 85 (FIG. 5) before it returns to the general sector between positions 1 and 15, namely before it returns to position 9 in the 7th step. Therefore, the six equipment units can be adequately placed around the circumference of the precessor wheel. With a larger shift, it is possible that fewer equipment units could be placed around the circumference of the precessor wheel and still operate as closely in time as do the photometer 112, the sample dispense unit 116, the sample mix unit 122 and the ISE unit 130. An increment for the large rotation shorter than 13 may require equipment units to be placed closer together.

In the preferred embodiment, six equipment units are used in the sample analyzer in addition to the load and unload units. With six equipment units at six different stations around the precessor wheel, and 90 sample holder positions, the quotient of 90 divided by 6 is 15. With the precessor wheel operating with cuvette pairs, the number of increments in each set n is 2. A small rotation provides a net increment of 1 leaving the large rotation with a net increment of 14 (15=14+1). An $S_{tot}$ of 15 does not meet the relationships of the foregoing equations, and therefore is not used if all 90 sample holder positions are to be used. A set of two increments which give a total shift of 16, with a large rotation having a net shift of 15 may be used because 16 does satisfy the foregoing equations. However, 14 would be a suitable number representing the sum of the net shifts of the large and small rotations, as discussed above. Depending on the size and number of the equipment units, a net shift for a large rotation of between 10 to 20 sample holder positions is adequate.

It can be determined by experimentation that there are a number of values for "$S_{tot}$" which satisfy the foregoing equations. While these values are theoretically possible, it will be understood that not all are practical for one reason or another. Values for "$S_{tot}$" which satisfy the foregoing equations include 2, 4, 8, 14, 16, 22, 26, 28, 32, 34, 38, 44, and so on, it being understood that the precessor wheel can advance two or reverse 88 and still operate in the same manner.

Typical reaction times for analyses to be conducted on such samples as human blood serum, plasma and the like is approximately 10 minutes. With a rotation time, including stationary time for both the large and small rotations of approximately 7½ seconds, wherein each cuvette is scanned once on every rotation, 10 minutes per reaction times 60 seconds per minute divided by 7.5 seconds per rotation gives approximately 80 rotations or 40 rotation pairs to insure that all reactions are complete before a given cuvette pair is unloaded. Therefore, unloading cuvette pairs after 42 rotation pairs is adequate. Additionally, operation within these parameters with 90 sample holder positions leaves empty sample holder positions for three rotation pairs for purposes of calibration.

Other characteristics of the specific embodiment described above with respect to FIGS. 4 and 5 will now be described. In the preferred embodiment, each cuvette pair spans eight degrees of arc on the precessor wheel. There is 3.395 degrees within a cuvette pair, center-to-center, and there is 4.605 degrees between cuvette pairs, center-to-center. The distance across a cuvette pair is preferably 0.943 inch. The distance between the centers of the cuvettes within a given pair is 0.4 inch, while the distance between the centers of the cuvettes between pairs is 0.543 inch. It takes 0.1163 seconds to traverse one cuvette pair and 0.04937 seconds to traverse center-to-center within a cuvette pair. It takes 0.06696 seconds to traverse center-to-center between cuvette pairs. The small and large rotations occur at the same angular velocity. The numbers provided herein assume that acceleration and deceleration times for all rotations are zero. A large rotation of 103 cuvette or sample holder positions rotates 51 cuvette pairs plus 1 between-pair distance. A small rotation of 91 cuvette or sample holder positions rotates 45 cuvette pairs plus 1 within-pair distance. A large rotation is 412.605 degrees and a small rotation is 363.395 degrees. A large rotation is completed in 6.0 seconds and a small rotation is completed in 5.2844 seconds. It takes 5.2350 seconds to complete one 360 degree rotation of the precessor wheel. The radius of the precessor wheel is preferably 8.75 inches.

Table I shows the relationships between the time duration from time equals zero to the angular displacement of the precessor wheel and the operations carried out by the various equipment units. The Table assumes that time zero is defined for a cuvette pair as the start of rotation immediately after that pair has been loaded onto the precessor wheel. As discussed above, the precessor wheel will make 45 rotation pairs before a given sample holder position returns to exactly the same position. The time to make these rotations is 675 seconds (45 rotation pairs times 15 seconds per rotation pair).

The temporal relationship between a cuvette pair and the cuvette pair next to it in a counterclockwise direction is $$T_{(i+1)\&(j+1)} = T_{i\&j} + 195 \text{ (seconds) mod } 675. \quad (10)$$

The shift of 195 seconds can be determined from the following relationships.

$$(\text{Displacement} \times N) \bmod \text{``}M\text{''} = I \quad (11)$$

where displacement is derived from the fact that every 15 seconds, 7 cuvette pairs are moved and "M" corresponds to 45 cuvette pairs. The desired index is 1, and the next cuvette is counterclockwise. Therefore, the equation becomes $$(7 \times N) \bmod 45 = 1, \text{ or} \quad (12)$$

$$N = (45*K+1)/7, \quad (13)$$

where "N" and "K" are integers. The smallest values of "K" and "N" which are solutions to this equation are K equals 2 and N equals 13. Multiplying "N" by the time required for indexing one pair is 13 times 15 or 195 seconds.

The Table I also shows a column indicating whether or not the precessor wheel is moving (M) or stopped (S) when the particular operation is accomplished. A column is also provided showing the rotation size, namely a large rotation of 103 sample holder positions or 91. The final column shows the step number corresponding to the step numbers identified in FIG. 5. It should be noted that only the large rotations are identified with the step size, such that the large and small rotations as a pair constitute one step. It also should be noted that the step number in Table I is positioned in the table opposite the rotation size which is about to occur as shown in the table.

Considering Table I, it can be seen that each cuvette is scanned by the photometer at least every 7.5 seconds and each of the first and second cuvettes after loading are presented to the photometer, the sample dispense unit, the sample mix unit the ISE unit, the reagent add I, and the reagent mix I unit within a minute and a half.

The above described apparatus and processes provides a method of determining the physical position of each sequential logical or temporal operation. The apparatus optimizes the use of mechanical equipment and also optimizes the number of mechanical operations occurring each time the precessor wheel stops. Once the desired relationship between the shift amounts, the number and location of mechanical equipment and the number of sample positions are determined, the location and sequence of all samples are known at any given time. Equipment units can be distributed around the precessor wheel or other conveyor system as necessary to provide the desired operations. Additionally, a full 360 degree rotation with each large and small rotation permits repeated scanning of every cuvette as it passes the photometer station.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

| Time (sec) (next) | Angular Disp from T = 0 | Operation | (M)oving or (S)topped | Rotation Size | Stop No. |
| --- | --- | --- | --- | --- | --- |
| 0 | 0 | finish load cuvette pair in position 8 and start rotate | M | 103 | 1 |
| 0.765 | 52.605 | read cuvette A | M | | |
| 0.814 | 56.0 | read cuvette B | M | | |
| 6.0 | 52.605 | stop rotate | S | | |
| | | read cuvette A | S | | |
| 7.5 | 52.605 | start rotate | M | 91 | |
| 7.549 | 56.0 | read cuvette B | M | | |
| 12.735 | 52.605 | read cuvette A | M | | |
| 12.784 | 56.0 | stop rotate | S | | |
| | | read cuvette B | S | | |
| 15.000 | 56.0 | start rotate | M | 103 | 2 |
| 20.186 | | read cuvette A | M | | |
| 20.235 | | read cuvette B | M | | |
| 21.000 | 108.605 | stop rotate | S | | |
| | | add sample to cuv A | | | |
| 22.500 | | start rotate | M | 91 | |
| 26.921 | | read cuvette A | M | | |
| 26.970 | | read cuvette B | M | | |
| 27.784 | 112.0 | stop rotate | S | | |
| | | add sample to cuv B | S | | |
| 30.000 | | start rotate | M | 103 | 3 |
| 34.371 | | read cuvette A | M | | |

-continued

| Time (sec) (next) | Angular Disp from T = 0 | Operation | (M)oving or (S)topped | Rotation Size | Stop No. |
|---|---|---|---|---|---|
| 34.421 | | read cuvette B | M | | |
| 36.000 | 164.605 | stop rotate | S | | |
| | | mix cuvette A | S | | |
| 37.500 | | start rotate | M | 91 | |
| 41.106 | | read cuvette A | M | | |
| 41.156 | | read cuvette B | M | | |
| 42.784 | 168.00 | stop rotate | S | | |
| | | mix cuvette B | S | | |
| 45.000 | | start rotate | M | 103 | 4 |
| 48.557 | | read cuvette A | M | | |
| 48.606 | | read cuvette B | M | | |
| 51.000 | 220.605 | stop rotate | S | | |
| | | ISE aspirate cuv A | S | | |
| 52.500 | | start rotate | M | 91 | |
| 55.292 | | read cuvette A | M | | |
| 55.341 | | read cuvette B | M | | |
| 57.784 | 224.0 | stop rotate | S | | |
| | | ISE aspirate cuv B | S | | |
| 60.000 | | start rotate | M | 103 | 5 |
| 62.743 | | read cuvette A | M | | |
| 62.792 | | read cuvette B | M | | |
| 66.000 | 276.605 | stop rotate | S | | |
| | | Rgt 1 add cuvette A | S | | |
| 67.500 | | start rotate | M | 91 | |
| 69.478 | | read cuvette A | M | | |
| 69.527 | | read cuvette B | M | | |
| 72.784 | 280.0 | stop rotate | S | | |
| | | Rgt 1 add cuvette B | S | | |
| 75.000 | | start rotate | M | 103 | 6 |
| 76.928 | | read cuvette A | M | | |
| 76.978 | | read cuvette B | M | | |
| 81.000 | 332.605 | stop rotate | S | | |
| | | Rgt 1 mix cuvette A | S | | |
| 82.500 | | start rotate | M | 91 | |
| 83.663 | | read cuvette A | M | | |
| 83.713 | | read cuvette B | M | | |
| 87.784 | 336.0 | stop rotate | S | | |
| | | Rgt 1 mix cuvette B | S | 103 | 7 |
| 90.000 | | start rotate | M | | |
| 91.114 | | read cuvette A | M | | |
| 91.163 | | read cuvette B | M | | |
| 96.000 | 28.605 | stop rotate | S | | |
| 97.500 | | start rotate | S | 91 | |
| 97.849 | | read cuvette A | M | | |
| 97.898 | | read cuvette B | M | | |
| 102.784 | 32.0 | stop rotate | S | | |
| 105.000 | | start rotate | S | 103 | 8 |
| 105.300 | | read cuvette A | M | | |
| 105.349 | | read cuvette B | M | | |
| 110.535 | | read cuvette A | M | | |
| 110.584 | | read cuvette B | M | | |
| 111.000 | 84.605 | stop rotate | S | | |
| 112.500 | | start rotate | M | 91 | |
| 117.270 | | read cuvette A | M | | |
| 117.319 | | read cuvette B | M | | |
| 117.784 | 88.0 | stop rotate | S | | |
| 120.000 | | start rotate | M | 103 | 9 |
| 124.720 | | read cuvette A | M | | |
| 124.770 | | read cuvette B | M | | |
| 126.000 | 140.605 | stop rotate | S | | |
| 127.500 | | start rotate | M | 91 | |
| 131.455 | | read cuvette A | M | | |
| 131.505 | | read cuvette B | M | | |
| 132.784 | 144.0 | stop rotate | S | | |
| 135.000 | | start rotate | M | 103 | 10 |
| 138.906 | | read cuvette A | M | | |
| 138.955 | | read cuvette B | M | | |
| 141.000 | 196.605 | stop rotate | S | | |
| 142.500 | | start rotate | M | 91 | |
| 145.641 | | read cuvette A | M | | |
| 145.690 | | read cuvette B | M | | |
| 147.784 | 200.0 | stop rotate | S | | |
| 150.000 | | start rotate | M | 103 | 11 |
| 153.092 | | read cuvette A | M | | |
| 153.141 | | read cuvette B | M | | |
| 156.000 | 252.605 | stop rotate | S | | |
| 157.500 | | start rotate | M | 91 | |
| 159.827 | | read cuvette A | M | | |
| 159.876 | | read cuvette B | M | | |

-continued

| Time (sec) (next) | Angular Disp from T = O | Operation | (M)oving or (S)topped | Rotation Size | Stop No. |
|---|---|---|---|---|---|
| 162.784 | 256.0 | stop rotate | S | | |
| 165.000 | | start rotate | M | 103 | 12 |
| 167.277 | | read cuvette A | M | | |
| 167.327 | | read cuvette B | M | | |
| 171.000 | 308.605 | stop rotate | S | | |
| 172.500 | | start rotate | M | 91 | |
| 174.012 | | read cuvette A | M | | |
| 174.062 | | read cuvette B | M | | |
| 177.784 | 312.0 | stop rotate | S | | |
| 180.000 | | start rotate | M | 103 | 13 |
| 181.463 | | read cuvette A | M | | |
| 181.512 | | read cuvette B | M | | |
| 186.000 | 4.605 | stop rotate | S | | |
| 187.500 | | start rotate | M | 91 | |
| 188.198 | | read cuvette A | M | | |
| 188.247 | | read cuvette B | M | | |
| 192.784 | 8.0 | stop rotate | S | | |
| 195.000 | | start rotate | M | 103 | 14 |
| 195.649 | | read cuvette A | M | | |
| 195.698 | | read cuvette B | M | | |
| 200.884 | | read cuvette A | M | | |
| 200.933 | | read cuvette B | M | | |
| 201.000 | 60.605 | stop rotate | S | | |
| 202.500 | | start rotate | M | 91 | |
| 207.619 | | read cuvette A | M | | |
| 207.668 | | read cuvette B | M | | |
| 207.784 | 64.0 | stop rotate | S | | |
| 210.000 | | start rotate | M | 103 | 15 |
| 215.069 | | read cuvette A | M | | |
| 215.119 | | read cuvette B | M | | |
| 216.000 | 116.605 | stop rotate | S | | |
| 217.500 | | start rotate | M | 91 | |
| 221.804 | | read cuvette A | M | | |
| 221.854 | | read cuvette B | M | | |
| 222.784 | 120.0 | stop rotate | S | | |
| 225.000 | | start rotate | M | 103 | 16 |
| 229.255 | | read cuvette A | M | | |
| 229.304 | | read cuvette B | M | | |
| 231.000 | 172.605 | stop rotate | S | | |
| 232.500 | | start rotate | M | 91 | |
| 235.990 | | read cuvette A | M | | |
| 236.039 | | read cuvette B | M | | |
| 237.784 | 176.0 | stop rotate | S | | |
| 240.000 | | start rotate | M | 103 | 17 |
| 243.441 | | read cuvette A | M | | |
| 243.490 | | read cuvette B | M | | |
| 246.000 | 228.605 | stop rotate | S | | |
| 247.500 | | start rotate | M | 91 | |
| 250.176 | | read cuvette A | M | | |
| 250.225 | | read cuvette B | M | | |
| 252.784 | 232.0 | stop rotate | S | | |
| 255.000 | | start rotate | M | 103 | 18 |
| 257.626 | | read cuvette A | M | | |
| 257.676 | | read cuvette B | M | | |
| 261.000 | 284.605 | stop rotate | S | | |
| | | Rgt 2 add cuvette A | S | | |
| 262.500 | | start rotate | M | 91 | |
| 264.361 | | read cuvette A | M | | |
| 264.411 | | read cuvette B | M | | |
| 267.784 | 288.0 | stop rotate | S | | |
| | | Rgt 2 add cuvette B | S | | |
| 270.000 | | start rotate | M | 103 | 19 |
| 271.812 | | read cuvette A | M | | |
| 271.861 | | read cuvette B | M | | |
| 276.000 | 340.605 | stop rotate | S | | |
| | | Rgt 2 mix cuvette A | S | | |
| 277.500 | | start rotate | M | 91 | |
| 278.547 | | read cuvette A | M | | |
| 278.596 | | read cuvette B | M | | |
| 282.784 | 344.0 | stop rotate | S | | |
| | | Rgt 2 mix cuvette B | S | | |
| 285.000 | | start rotate | M | 103 | 20 |
| 285.998 | | read cuvette A | M | | |
| 286.047 | | read cuvette B | M | | |
| 291.000 | 36.605 | stop rotate | S | | |
| 292.500 | | start rotate | M | 91 | |
| 292.733 | | read cuvette A | M | | |
| 292.782 | | read cuvette B | M | | |
| 297.784 | 40.0 | stop rotate | S | | |

-continued

| Time (sec) (next) | Angular Disp from T = O | Operation | (M)oving or (S)topped | Rotation Size | Stop No. |
|---|---|---|---|---|---|
| 300.000 | | start rotate | M | 103 | 21 |
| 300.183 | | read cuvette A | M | | |
| 300.233 | | read cuvette B | M | | |
| 305.418 | | read cuvette A | M | | |
| 305.468 | | read cuvette B | M | | |
| 306.000 | 92.605 | stop rotate | S | | |
| 307.500 | | start rotate | M | 91 | |
| 312.153 | | read cuvette A | M | | |
| 312.203 | | read cuvette B | M | | |
| 312.784 | 96.0 | stop rotate | S | | |
| 315.000 | | start rotate | M | 103 | 22 |
| 319.604 | | read cuvette A | M | | |
| 319.653 | | read cuvette B | M | | |
| 321.000 | 148.605 | stop rotate | S | | |
| 322.500 | | start rotate | M | 91 | |
| 326.339 | | read cuvette A | M | | |
| 326.388 | | read cuvette B | M | | |
| 327.784 | 152.0 | stop rotate | S | | |
| 330.000 | | start rotate | M | 103 | 23 |
| 333.790 | | read cuvette A | M | | |
| 333.839 | | read cuvette B | M | | |
| 336.000 | 204.605 | stop rotate | S | | |
| 337.500 | | start rotate | M | 91 | |
| 340.525 | | read cuvette A | M | | |
| 340.574 | | read cuvette B | M | | |
| 342.784 | 208.0 | stop rotate | S | | |
| 345.000 | | start rotate | M | 103 | 24 |
| 347.975 | | read cuvette A | M | | |
| 348.025 | | read cuvette B | M | | |
| 351.000 | 260.605 | stop rotate | S | | |
| 352.500 | | start rotate | M | 91 | |
| 354.710 | | read cuvette A | M | | |
| 354.760 | | read cuvette B | M | | |
| 357.784 | 265.0 | stop rotate | S | | |
| 360.000 | | start rotate | M | 103 | 25 |
| 362.161 | | read cuvette A | M | | |
| 362.210 | | read cuvette B | M | | |
| 366.000 | 316.605 | stop rotate | S | | |
| 367.500 | | start rotate | M | 91 | |
| 368.896 | | read cuvette A | M | | |
| 368.945 | | read cuvette B | M | | |
| 372.784 | 320.0 | stop rotate | S | | |
| 375.000 | | start rotate | M | 103 | 26 |
| 376.347 | | read cuvette A | M | | |
| 376.396 | | read cuvette B | M | | |
| 381.000 | 12.605 | stop rotate | S | | |
| 382.500 | | start rotate | M | 91 | |
| 383.082 | | read cuvette A | M | | |
| 383.131 | | read cuvette B | M | | |
| 387.784 | 16.0 | stop rotate | S | | |
| 390.000 | | start rotate | M | 103 | 27 |
| 390.532 | | read cuvette A | M | | |
| 390.582 | | read cuvette B | M | | |
| 395.767 | | read cuvette A | M | | |
| 395.817 | | read cuvette B | M | | |
| 396.000 | 68.605 | stop rotate | S | | |
| 397.500 | | start rotate | M | 91 | |
| 402.502 | | read cuvette A | M | | |
| 402.552 | | read cuvette B | M | | |
| 402.784 | 72.0 | stop rotate | S | | |
| 405.000 | | start rotate | M | 103 | 28 |
| 409.953 | | read cuvette A | M | | |
| 410.002 | | read cuvette B | M | | |
| 411.000 | 124.605 | stop rotate | S | | |
| 412.500 | | start rotate | M | 91 | |
| 416.688 | | read cuvette A | M | | |
| 416.737 | | read cuvette B | M | | |
| 417.784 | 128.0 | stop rotate | S | | |
| 420.000 | | start rotate | M | 103 | 29 |
| 424.139 | | read cuvette A | M | | |
| 424.188 | | read cuvette B | M | | |
| 426.000 | 180.605 | stop rotate | S | | |
| 427.500 | | start rotate | M | 91 | |
| 430.874 | | read cuvette A | M | | |
| 430.923 | | read cuvette B | M | | |
| 432.784 | 184.0 | stop rotate | S | | |
| 435.000 | | start rotate | M | 103 | 30 |
| 438.324 | | read cuvette A | M | | |
| 438.374 | | read cuvette B | M | | |

-continued

| Time (sec) (next) | Angular Disp from T = O | Operation | (M)oving or (S)topped | Rotation Size | Stop No. |
|---|---|---|---|---|---|
| 441.000 | 236.605 | stop rotate | S | | |
| 442.500 | | start rotate | M | 91 | |
| 445.059 | | read cuvette A | M | | |
| 445.109 | | read cuvette B | M | | |
| 447.784 | 240.0 | stop rotate | S | | |
| 450.000 | | start rotate | M | 103 | 31 |
| 452.510 | | read cuvette A | M | | |
| 452.559 | | read cuvette B | M | | |
| 456.000 | 292.605 | stop rotate | S | | |
| 457.500 | | start rotate | M | 91 | |
| 459.245 | | read cuvette A | M | | |
| 459.294 | | read cuvette B | M | | |
| 462.784 | 296.0 | stop rotate | S | | |
| 465.000 | | start rotate | M | 103 | 32 |
| 466.696 | | read cuvette A | M | | |
| 466.745 | | read cuvette B | M | | |
| 471.000 | 348.605 | stop rotate | S | | |
| 472.500 | | start rotate | M | 91 | |
| 473.431 | | read cuvette A | M | | |
| 473.480 | | read cuvette B | M | | |
| 477.784 | 352.0 | stop rotate | S | | |
| 480.000 | | start rotate | M | 103 | 33 |
| 480.881 | | read cuvette A | M | | |
| 480.931 | | read cuvette B | M | | |
| 486.000 | 44.605 | stop rotate | S | | |
| 487.500 | | start rotate | M | 91 | |
| 487.616 | | read cuvette A | M | | |
| 487.666 | | read cuvette B | M | | |
| 492.784 | 48.0 | stop rotate | S | | |
| 495.000 | | start rotate | M | 103 | 34 |
| 495.067 | | read cuvette A | M | | |
| 495.116 | | read cuvette B | M | | |
| 500.302 | | read cuvette A | M | | |
| 500.351 | | read cuvette B | M | | |
| 501.000 | 100.605 | stop rotate | S | | |
| 502.500 | | start rotate | M | 91 | |
| 507.037 | | read cuvette A | M | | |
| 507.086 | | read cuvette B | M | | |
| 507.784 | 104.0 | stop rotate | S | | |
| 510.000 | | start rotate | M | 103 | 35 |
| 514.488 | | read cuvette A | M | | |
| 514.537 | | read cuvette B | M | | |
| 516.000 | 156.605 | stop rotate | S | | |
| 517.500 | | start rotate | M | 91 | |
| 521.223 | | read cuvette A | M | | |
| 521.272 | | read cuvette B | M | | |
| 522.784 | 160.0 | stop rotate | S | | |
| 525.000 | | start rotate | M | 103 | 36 |
| 528.673 | | read cuvette A | M | | |
| 528.723 | | read cuvette B | M | | |
| 531.000 | 212.605 | stop rotate | S | | |
| 532.500 | | start rotate | M | 91 | |
| 535.408 | | read cuvette A | M | | |
| 535.458 | | read cuvette B | M | | |
| 537.784 | 216.0 | stop rotate | S | | |
| 540.000 | | start rotate | M | 103 | 37 |
| 542.859 | | read cuvette A | M | | |
| 542.908 | | read cuvette B | M | | |
| 546.000 | 268.605 | stop rotate | S | | |
| 547.500 | | start rotate | M | 91 | |
| 549.594 | | read cuvette A | M | | |
| 549.643 | | read cuvette B | M | | |
| 552.784 | 272.0 | stop rotate | S | | |
| 555.000 | | start rotate | M | 103 | 38 |
| 557.045 | | read cuvette A | M | | |
| 557.094 | | read cuvette B | M | | |
| 561.000 | 324.605 | stop rotate | S | | |
| 562.500 | | start rotate | M | 91 | |
| 563.780 | | read cuvette A | M | | |
| 563.829 | | read cuvette B | M | | |
| 567.784 | 328.0 | stop rotate | S | | |
| 570.000 | | start rotate | M | 103 | 39 |
| 571.230 | | read cuvette A | M | | |
| 571.280 | | read cuvette B | M | | |
| 576.000 | 20.605 | stop rotate | S | | |
| 577.500 | | start rotate | M | 91 | |
| 577.965 | | read cuvette A | M | | |
| 578.015 | | read cuvette B | M | | |
| 582.784 | 24.0 | stop rotate | S | | |

-continued

| Time (sec) (next) | Angular Disp from T = O | Operation | (M)oving or (S)topped | Rotation Size | Stop No. |
|---|---|---|---|---|---|
| 585.000 | | start rotate | M | 103 | 40 |
| 585.416 | | read cuvette A | M | | |
| 585.465 | | read cuvette B | M | | |
| 590.651 | | read cuvette A | M | | |
| 590.700 | | read cuvette B | M | | |
| 591.000 | 76.605 | stop rotate | S | | |
| 592.500 | | start rotate | M | 91 | |
| 597.386 | | read cuvette A | M | | |
| 597.435 | | read cuvette B | M | | |
| 597.784 | 80.0 | stop rotate | S | | |
| 600.000 | | start rotate | M | 103 | 41 |
| 604.837 | | read cuvette A | M | | |
| 604.886 | | read cuvette B | M | | |
| 606.000 | 132.605 | stop rotate | S | | |
| 607.500 | | start rotate | M | 91 | |
| 611.572 | | read cuvette A | M | | |
| 6121.621 | | read cuvette B | M | | |
| 612.784 | 136.0 | stop rotate | S | | |
| 615.000 | | start rotate | M | 103 | 42 |
| 619.022 | | read cuvette A | M | | |
| 619.072 | | read cuvette B | M | | |
| 621.000 | 188.605 | stop rotate | S | | |
| 622.500 | | start rotate | M | 91 | |
| 625.757 | | read cuvette A | M | | |
| 625.807 | | read cuvette B | M | | |
| 627.784 | 192.0 | stop rotate | S | | |
| | | cuvette pair removed | S | | |
| 630.000 | | start rotate | M | 103 | 43 |
| 633.208 | | read cuvette A | M | | |
| 633.257 | | read cuvette B | M | | |
| 636.000 | 244.605 | stop rotate | S | | |
| 637.500 | | start rotate | M | 91 | |
| 639.943 | | read cuvette A | M | | |
| 639.992 | | read cuvette B | M | | |
| 642.784 | 248.0 | stop rotate | S | | |
| 645.000 | | start rotate | M | 103 | 44 |
| 647.394 | | read cuvette A | M | | |
| 647.443 | | read cuvette B | M | | |
| 651.000 | 300.605 | stop rotate | S | | |
| 652.500 | | start rotate | M | 91 | |
| 654.129 | | read cuvette A | M | | |
| 654.178 | | read cuvette B | M | | |
| 657.784 | 304.0 | stop rotate | S | | |
| 660.000 | | start rotate | M | 103 | 45 |
| 661.579 | | read cuvette A | M | | |
| 661.629 | | read cuvette B | M | | |
| 666.000 | 356.605 | stop rotate | S | | |
| 667.500 | | start rotate | M | 91 | |
| 668.314 | | read cuvette A | M | | |
| 668.364 | | read cuvette B | M | | |
| 672.784 | 360.0 | stop rotate | S | | |
| | | cuvette pair inserted | S | | |
| 675.0 | | start rotate | M | 103 | 1 |

We claim:

1. A sample analyzer for analyzing a plurality of samples, the analyzer comprising:
   a movable sample support for holding M samples arranged in M sample holders in a sequence for movement in a first direction, said samples being arranged in g groups with n samples in each group so that M equals the product of g and n;
   an indexing drive means for moving the samples in sample support in the first direction as a sequence of primary shifts and, for n>1, secondary shifts, in which:
   each primary shift is a net movement of the sample support in the first direction by P sample holder positions from a current sample group;
   each secondary shift is a net movement of the sample support within the current sample group;
   the values P and M are relatively prime, that is, they have no factors in common other than unity;
   the greatest common factor between the value (P+n−1) and M is n;
   whereby each of the g groups is the current group once before the sample support returns to an initial position.

2. The analyzer of claim 1 wherein the sample support is substantially round and rotatable in a circle to present a sample to at least one activity station.

3. The analyzer of claim 2 wherein the sample support has a radius of approximately 8.7 inches.

4. The analyzer of claim 2 wherein the sample holders are grouped into forty-five pairs, each spanning an arc of approximately eight degrees.

5. The analyzer of claim 4 wherein
   the primary shift corresponds to a rotation of the sample support of approximately 412 degrees and
   there is a single secondary shift for each group corresponding a rotation of the sample support of approximately 363 degrees and wherein the sample support includes a first sample position which rotates from and returns to a given position after forty-five pairs of rotations.

6. The analyzer of claim 1 wherein M=90, P=103, and each secondary shift corresponds to a movement of the sample holder by 91 sample positions.

7. The analyzer of claim 1, further including a photometer positioned relative to the sample support so as to analyze a characteristic of the sample whenever a sample is passed before the photometer, and further including means for analyzing a characteristic of each sample for every advance of the sample support.

8. The analyzer of claim 1, further comprising:
a sample load station positioned at a first position relative to the sample support; and
a plurality of operations stations distributed in the first direction in a spatial sequence substantially uniformly about the movable sample support at defined positions spaced sequentially in the first direction from the sample load station such that a given sample to be presented in a time sequence to each operations station is presented to at least one operations station in a time sequence different from the spatial sequence of the operations stations.

9. The sample analyzer of claim 8 wherein the sample support has 90 sample holders, and wherein the analyzer further includes six operations stations including the sample load station.

10. The apparatus of claim 2, wherein each primary and secondary shift constitutes a movement of at least 360 degrees.

11. The apparatus as claimed in claim 1 further comprising an empty sample container insert assembly and a sample scanner spaced from the empty sample container insert assembly wherein a spacing between the insert assembly and the sample scanner corresponds to a number of intervening holders such that a single movement of the indexing drive means places an empty sample container from the insert assembly before the scanner to be scanned.

12. The apparatus of claim 11 further comprising a sample add station wherein the sample add station is separated from the sample scanner a distance corresponding to 13 sample holder positions.

13. The apparatus of claim 11 wherein the indexing drive means is a 90 position circular wheel for holding sample holders, wherein the sample holders are arranged about the circumference of the circular wheel and further comprising a plurality of stations distributed about the circumference of the wheel and wherein each station comprises a separate space corresponding to approximately 15 sample holder positions and wherein each station includes an operating apparatus positioned so as to operate at a sample holder corresponding to one of the 15 positions.

14. The apparatus of claim 13 further comprising stations distributed about the wheel and having an empty sample container insert assembly and wherein a sample holder in the wheel is not presented to all stations in sequential positional order as the wheel rotates and presents a sample holder to stations.

15. The apparatus of claim 14 further comprising two operations stations and a cuvette unload station wherein the cuvette unload station is placed physically between the two operations stations about the circumference of the wheel.

16. The apparatus of claim 14 further comprising a sample dispensing station, a mixing station, a detection station, a reagent mixing station, and a reagent adding station wherein the empty sample container insert assembly is approximately 15 sample holder positions away from the sample scanner station, the sample dispense station is approximately 15 sample holders away from the sample scanner station, the sample mixing station is approximately 15 sample holder positions away from the sample dispense station, the read station is approximately 15 sample holder positions away from the sample mix station and the reagent add station is approximately 15 sample holder positions away from the read station.

17. The apparatus as claimed in claim 11 wherein the indexing drive means is timed to complete a cycle in approximately 10 minutes.

18. The apparatus of claim 11 comprising a plurality of stations, two of which are the empty sample container insert assembly and the sample scanner, wherein the empty sample container insert assembly is positioned next to the movable sample support and wherein the empty sample container insert assembly is positioned in an area subtended by an arc approximately equivalent to 15 sample holder positions and wherein a sample holder inserted by the empty sample container insert assembly stops at approximately six operating stations other than the empty sample container insert assembly and the sample scanner before returning to the empty sample container insert assembly area.

19. A method for controlling an analyzer for a plurality of samples comprising the steps of:
A) in a movable sample support, arranging M samples in M sample holders in g groups with n samples in each group, so that M equals the product of g and n;
B) moving the samples in the sample support in a first direction as a sequence of primary shifts;
C) for n>1, further moving the samples in the sample support in as a sequence of secondary shifts, in which:
D) each primary shift is a net movement of the sample support in the first direction by P sample holder positions from a current sample group;
E) each secondary shift is a net movement of the sample support within the current sample group;
F) the values P and M are relatively prime, that is, they have no factors in common other than unity;
G) the greatest common factor between the value (P+n−1) and M is n;
whereby each of the g groups is the current group once before the sample support returns to an initial position.

20. A method as defined in claim 19, further including the following step:
for each primary and secondary shift, moving each sample past a detector by moving the sample holder by more than M sample holder positions.

* * * * *